United States Patent [19]

Berger

[11] Patent Number: 4,566,949

[45] Date of Patent: Jan. 28, 1986

[54] METHOD OF OPERATING A SELF CLEANING ELECTROCHEMICAL DETECTOR

[75] Inventor: Terry A. Berger, Landenberg, Pa.

[73] Assignee: Hewlett-Packard Company, Palo Alto, Calif.

[21] Appl. No.: 659,792

[22] Filed: Oct. 11, 1984

Related U.S. Application Data

[62] Division of Ser. No. 543,663, Oct. 19, 1983, Pat. No. 4,496,454.

[51] Int. Cl.$^4$ .............................................. G01N 30/62
[52] U.S. Cl. .................................. 204/1 T; 73/61.1 C; 204/402
[58] Field of Search ................ 204/1 T, 402, 406, 409, 204/411, 412, 70; 436/161; 73/61.1 C; 324/425

[56] References Cited

U.S. PATENT DOCUMENTS

| 3,676,321 | 7/1972 | Cummings et al. | 204/412 X |
| 4,057,478 | 11/1977 | Bruckenstein et al. | 204/402 |
| 4,059,406 | 11/1977 | Fleet | 204/1 T X |

FOREIGN PATENT DOCUMENTS 2079474  1/1982  United Kingdom ................ 204/402

OTHER PUBLICATIONS

Joseph Yamada and Hiroaki Matsuda, "Wall Jet Electrodes", Electroanalytical Chemistry and Interfacial Electrochemistry, 44, p. 189, (1973).

Primary Examiner—G. L. Kaplan
Attorney, Agent, or Firm—Jeffery B. Fromm

[57] ABSTRACT

An improved electrochemical cell and detector which is especially suited for analysis of rapidly changing flowing streams such as found in high performance liquid chromatography is disclosed. A uniquely designed jet made of microbore drawn capillary tubing permits the construction of a cell for very low flow rates that still retains true wall-jet hydrodynamics. The invention prevents changes in cell response in time by periodically cleaning a working electrode in a novel way. Cleaning and detection are both accomplished on a time scale much shorter than the fastest liquid chromatograph peaks by means of a unique three electrode cell design utilizing a small diameter, low capacitance, metal working electrode situated close to a reference electrode. Cleaning is accomplished by means of a non-square wave periodic waveform which is effective in cleaning a wide variety of contaminants through the oxidation and reduction of the working electrode and/or solvent prior to application of one or more working potentials while providing a stable, reproducible detector. The detector thus provides improvements in both sensitivity and bandwidth over the prior art.

11 Claims, 17 Drawing Figures

METHOD OF OPERATING A SELF CLEANING ELECTROCHEMICAL DETECTOR

This is a division of application Ser. No. 543,663 filed Oct. 19, 1983 and now U.S. Pat. No. 4,496,454.

BACKGROUND

The use of electrochemical (EC) detectors for liquid chromatography (LC) is a growing field. The primary use of such detectors is for trace analysis offering up to four orders of magnitude increased sensitivity over the commonly used ultraviolet-visible (UV-VIS) photometer. Other possible advantages of EC detectors include increased selectivity, similar response to equal concentrations of electroactive species and relatively inexpensive hardware.

Despite these apparent advantages, EC detectors have not achieved widespread routine use for a number of reasons. Response is achieved by electrochemically oxidizing or reducing electroactive species in the chromatographic eluent on the cell working electrode (WE) at potentials characteristic of the species. The current that flows at a given potential is proportional to the sample concentration and the hydrodynamic pattern of the cell. Many compounds yield reaction products which form passivating films on the WE surface thereby changing detector response with time. Such fouling can be quite rapid, allowing as little as four hours of operation with continuously decreasing response, after which the cell must be disassembled and the WE surface renewed. Reassembly and equilibration back to near steady state background current may then require as much as 24 hours before trace analysis can resume. Continuously changing response and extensive skilled maintenance are very unattractive and expensive to the routine user. A number of schemes have been attempted to prevent or minimize fouling. Mechanical scrapers produce noisy signals due to variations in the exposed surface area of the electrode and compromise the response volume requirements of the cell. A dropping mercury electrode is difficult to miniaturize and due to the ease of oxidation of mercury is really only useful for electrochemical reductions. Both techniques attempt to mechanically renew the electrode surface on a short time scale compared to the analysis time.

Continuous calibration with internal standards does not solve the problem but does allow reasonably accurate analysis during the relatively short lifetime of the electrode surface. As the electrode fouls, the signal to noise ratio falls and there is an increased chance of sample contamination with addition of the standard.

Very low concentrations of normally fouling species tend not to foul due to the low surface coverage and lack of interaction on the electrode surface. Fouling may then be prevented if extensive sample pretreatment removes or greatly dilutes offending species without substantially changing the species of interest. This may require substantial method development, create sample recovery or contamination problems, and increase analysis time and cost.

As demonstrated by Fleet in U.S. Pat. No. 4,059,406 issued Nov. 22, 1977, other workers have attempted to desorb offending species before the surface coverage built up to critical levels by changing the potential of the working electrode periodically to one where the specie desorbs. Unfortunately, many troublesome chemical species are very strongly adsorbed and do not significantly desorb at potentials where the electrode and/or the solution is not strongly oxidized or reduced. In addition the kinetics of such desorption may be too slow to be of practical use in cleaning and such a desorption method is very specific so a new method must be developed for each set of analytical conditions. The use of such a method with large electrodes requires relatively high power electronics to charge the WE capacitance when large potential steps are made.

Any EC detector should be optimized in three ways. The chromatographic peaks should not be substantially diluted or distorted by the cell, the electrode configuration should yield undistorted electrochemical performance and the cell internal geometry should produce an optimum undistorted hydrodynamic pattern maximizing response at LC flow rates. Prior EC LC detectors have not satisfied all of these requirements.

Optimum LC conditions for trace analysis are somewhat different than those used for more routine higher concentration analysis. Separations should be optimized to achieve very small values of the column solute capacity factor (i.e., k' should be approximately 0.5–1.5) with isocratic conditions to minimize sample dilution and background slope. The column should use the smallest diameter packing material available, the largest internal diameter (ID), and the shortest length consistent with the resolution required and sample size available. The volumetric flow rate through the column should provide the highest linear velocity consistent with the resolution required and the pumping system pressure capability. The injection volume should be the maximum consistent with the column capacity.

Under these conditions conventional 4.6 millimeters ID columns with 3 micrometer diameter column packing operated at optimum linear velocity should allow complete analysis of up to 24 components in less than 4.5 minutes with the widest peak 6.25 seconds across the base. By increasing linear velocity to 5 times optimum, the widest peak drops to 1.6 seconds across the base with a peak volume of 0.12 milliliters. Analysis time also drops by a factor of 5 to less than one minute. The fastest peak will then be less than 1 second across the base with a peak volume less than 80 microliters.

Smaller diameter columns are an important new area of LC technology. The primary advantages of such columns are much lower solvent consumption and much smaller sample size requirements. Such columns perform the same as conventional columns except peak volumes of even the longest retained peak can be as small as 4 microliters.

In order for an electrochemical detector to follow such an analysis without severe attenuation or peak distortion, the cell response volume should be in the range 0.1 to 8 microliters depending on the column used, and the detector time constant should be less than 200 milliseconds. Further, detector sensitivity should not be compromised to achieve such a fast response time.

The greatest effort in LC detector cell design has been placed in minimizing cell response volume and cells have been built with response volumes as low as 1 nanoliter. Achieving low dead volume is made difficult by the fact that it is often impossible to machine components of the sizes required since they are below the tolerances of machine tools. Fabrication techniques and cell geometries have evolved which achieve the desired response volume but at the expense of electrochemical and/or hydrodynamic performance.

SUMMARY OF THE INVENTION

A nearly ideal electrochemical cell should use a three electrode configuration composed of a current path between a working (WE) and a counter electrode (CE), and a potential feedback path between a reference electrode (RE) located very near the WE, and the potential control electronic circuitry which applies a potential to the CE. Solution resistance produces a voltage (IR) drop between the WE and CE which reduces the effective potential difference between the electrodes. The RE provides a means to compensate for most of this IR drop and maintain the relative potential of the WE very near the desired value.

The RE-WE separation distance should be very small (<<5 millimeters) to minimize uncompensated cell resistance (Ru). The RE should, however, not shield any part of the WE surface or interfere with the cell hydrodynamics. In addition, the RE internal filling solution should not contaminate the sample solution coming in contact with the WE.

The CE should be located symmetrically about and separated from the WE by a distance at least twice the WE-RE separation distance. This arrangement provides a uniform electric field and equipotential surface across the WE. This results in a current density distribution on the WE which is determined solely by the cell hydrodynamic pattern thus allowing comparison between theory and experimental results. Deviations in current density distribution will only result in decreased total current for a given electrode area.

Previously, LC EC cells almost universally placed the RE a substantial distance from the WE (up to 5 centimeters) and locate the CE very asymetrically relative to the WE and RE. Such an arrangement yields relatively poor potential control of the WE, distorts current density profiles and lowers the signal current for a given electrode area, concentration and hydrodynamic pattern. A further handicap of such an arrangement is that the potential of the WE cannot be changed rapidly since the large uncompensated cell resistance (Ru) is part of the RC time constant of the cell. The WE to solution interface produces a capacitance on the order of 10 to 100 microfarads/square centimeter, and charging current must flow through the cell when its potential is changed. Since the maximum current is determined primarily by the Ru and magnitude of the potential step, the time to completely charge the capacitance is determined by those factors plus the value of RuC. For larger electrodes and Ru values this time can be quite large making it practically impossible to change potential during the emergence of an LC peak.

Optimization of the cell hydrodynamics with the flow rates and peak characteristics dictated by the chromatographic separation has also been severely hampered by the difficulty in fabricating cells reproducibly due to the extremely small dimensions involved.

A comparison of tubular, thin film, stagnant flow and wall-jet hydrodynamics indicates that the wall-jet configuration should yield the highest dependence of signal on the average linear velocity of solution striking the WE. Yamada and Matsuda, in "Wall Jet Electrodes", Electroanalytical Chemistry and Interfacial Electrochemistry, 44, p. 189 (1973), developed the theory for and empirically demonstrated wall-jet hydrodynamics in flow cells but state that such hydrodynamics cannot be achieved with WE's of radius less than about 1.5 millimeters. The minimum cell volume with such a cell is approximately 0.8 microliters. Others have built true wall-jet cells but only with larger radius electrodes. Commercial detector cells exist which are called wall-jets and several workers have reported cells constructed using much smaller electrodes which are called wall-jets but the observed response indicates that these cells are actually thin layer, radial convection cells.

The failure to achieve wall jet hydrodynamics with small electrodes (i.e., <1.5 millimeters in radius) is due in part to the methods attempted to fabricate the cells. Further, Yamada and Matsuda misinterpreted part of their experimental results which has not been previously recognized by workers in the field. In FIG. 7, page 196 of Yamada and Matsuda's article in Electroanalytical Chemistry and Interfacial Electrochemistry, 44 (1973), the exhibited curves show a break in slope as electrode radius decreases below approximately 1.5 millimeters. Yamada and Matsuda interpret this to mean that wall jet hydrodynamics cannot be scaled below this value. There is actually an uncontrolled parameter which does not appear in the equation defining wall jet response but which can disrupt the hydrodynamic pattern. For small (1.5 millimeter radius) electrodes the jet outside diameter appears to be large compared to the WE diameter and protrudes into the space where the flow profile should be developing. Tests show no inherent lower limit of WE radius on which wall jet hydrodynamics can be established provided the jet OD is less than or equal to the electrode radius. Other workers in the field who have designed cells which attempt, but do not achieve wall jet hydrodynamics, have also ignored jet OD and have actually attempted to extend wall jet theory to include a jet consisting of an orifice through a flat plate located parallel to and very near the working electrode. Such a geometry results in thin layer hydrodynamics with radial convection if the orifice and WE are coaxial.

Signal to noise ratio (S/N) and system bandwidth are the ultimate determiners of any electrochemical detector's sensitivity. The signal per unit concentration is a function of cell geometry and hydrodynamics plus the bandwidth of the electronics measuring the current. System noise can have several sources in the bandwidth of interest in LC detection. An optimized detector should display maximum response and minimum noise in the range of 0.01 to 10 Hz to follow peaks 1 to 10 seconds across the base.

An annoying source of noise with EC detectors is short term variation in flow rate due to pump pulsations since the detectors are flow rate sensitive. By careful design of the LC solvent delivery system or synchronous detection this problem can be minimized. A more fundamental noise source is due to the interaction of the WE capacitance and voltage noise sources in the detector electronics. There has been a suggestion that the system noise in the frequency range of interest is proportional to the potentiostat output voltage noise. A deeper analysis reveals that electrometer output voltage noise (system noise) is proportional to electrode capacitance, electrometer feedback capacitance and the sum of potentiostat output voltage noise and electrometer input voltage noise. The ratio of electrode to feedback capacitance determines the amplification factor for the voltage noise level of the electronics. The standard technique for reducing system noise in the low frequency region is to use a large (i.e., 0.47 microfarad) feedback capacitor on the electrometer. Since a typical value for the electrometer feedback resistor is 10 megaohms the electrometer RC time constant becomes 4.7 seconds, much too slow to follow modern LC peaks. Decreasing the feedback capacitance to yield a time constant of 200 milliseconds unfortunately increases system noise by a factor of about 25.

The capacitance of the WE is proportional to the electrode surface area. Decreasing the electrode surface area decreases electrode capacitance and the required feedback capacitance to maintain a constant noise density. Since the feedback resistor remains fixed, the electrometer RC time constant can be decreased while maintaining the same noise level. At constant volumetric flow and velocity, the signal also decreases with decreasing surface area.

The present invention is an improvement in electrochemical detectors used for the analysis of flowing streams such as employed in modern liquid chromatography. The invention consists of two parts, a miniature flow cell and an electronic controller optimized for use with this cell. The cell exhibits true wall jet hydrodynamics with a working electrode smaller than 1.5 millimeters in radius. Further, the cell is a flow cell having response volume below 1 microliter and provides an optimum orientation of electrodes by which cell resistance (RC), uncompensated resistance (RU) and WE double layer capacitance (CDL) are optimized individually and to each other to yield fast response with low power consumption and low noise while maintaining a uniform electric field across the WE. The cell uses a unique column to cell transfer line which also acts as the hydrodynamic jet. The geometry and orientation of this jet is a major factor in achieving the desired hydrodynamic pattern in the cell and also results in a higher than normal response factor compared to the prior art.

The near ideal response of the present cell due to undistorted hydrodynamics and electrochemical performance has allowed identification of a major previously unreported noise source present in all electrochemical cells which is normally masked by nonideal cell response. The invention offers a means to minimize this noise source while increasing the cell response factor, increasing sensitivity at typical volumetric flow rates of chromatographic columns. The invention also provides a means to increase system bandwidth adequate to follow even the fastest LC peak while enhancing sensitivity over previous detectors. Bandwidth and sensitivity can be traded off against each other to allow even higher sensitivity if so desired.

The invention can also prevent changes in detector response with time due to fouling of the WE by electrochemical reaction products. The WE is periodically cleaned on a time scale much shorter than the fastest LC peak. Cleaning is accomplished through multiple mechanisms assuring a high probability that all fouling species can be cleaned.

A further advance in electrochemical detector design is in the ability to measure current to voltage relationships at multiple applied potentials on a time scale short compared to the time scale of eluting peaks. The invention eliminates redundant sets of components required in previous solutions to this problem.

The electrochemical cell employs a working electrode shaped like a disk of small surface area to minimize the CDL of the WE. The RE is located very near the WE, (i.e., 1 millimeter), minimizing RU while not interfering with the hydrodynamic pattern of the flowing stream or contaminating the surface of the WE with the RE internal filling solution. The large surface area CE is located symmetrically about the WE and separated from it by a distance at least three times the WE to RE separation distance. The electrode orientation insures very fast, undistorted electrochemical cell performance with a uniform electric field across the WE. A small bore capillary tube acts as the column to cell flow interconnection and serves as the jet for the wall jet cell. The jet should have a relatively low aspect ratio (outside diameter (OD)/inside diameter (ID)) less than or equal to four, to retain wall jet hydrodynamics and should penetrate the cell wall opposite the WE to direct a stream of fluid normal to and coaxially with the working electrode. The jet exit can therefore be positioned very near the WE surface without shielding it. The jet ID, WE diameter and jet to WE separation distance define the response volume of the cell which takes the form of a truncated cone, and is very small and independent of the dead volume of the cell compartment holding the three electrodes. The separation distance can be varied over the range of 0.25 to 20 times the jet ID without substantially changing detector response. The relatively large geometry of the cell compartment and a large diameter exit or waste outlet tube assures minimal pressure drop across the cell. Detector response at the flow rates characteristic of modern LC is enhanced by making the jet internal diameter very small (i.e., less than 250 micrometers, and typically 50 to 100 micrometers) greatly increasing the average linear velocity of the fluid exiting the jet (i.e., 100 to 1000 centimeters/second) compared to that exiting more conventional LC tubing or transfer lines (i.e., 8 centimeters/second. This is possible without plugging the tubing with particulates present in the fluid if the jet is formed by drawing fused silica or glass to the desired size capillary. A preferred embodiment of the jet in the present invention uses specially drawn fused silica capillaries with extremely smooth internal surfaces with surface features which are undetectable with a measurement resolution of 1000 Angstroms. The WE is made as small as possible to compliment the internal diameter of the jet. Wall jet response is achieved whenever the ratio of WE radius (R) to jet ID (a) is set above approximately four (provided the jet aspect ratio is also below approximately 4). If R/a is made much greater than 4, the outer rim of the electrode will operate at substantially lower current density than the inner region of the electrode. Since noise is proportional to electrode surface area, the maximum signal to noise ratio (S/N) is achieved with the smallest electrode area exhibiting wall jet response for a given jet ID. The smaller the jet, the higher the response per unit area of WE. The minimum jet size is limited by the pressure capability of the pumping system and the size of potentially plugging particles in the fluid. The smaller the WE area, the higher the potential sensitivity of the detector. If the ratio R/a is made much less than 4, response changes to that expected for stagnant flow hydrodynamics, the fraction of sample molecules which undergo reaction falls and signal per unit concentration decreases, resulting in lower S/N and a less sensitive detector.

The use of very small area electrodes results in very low CDL compared to most conventional flow cells (i.e., <1 microfarad compared to conventional values of 10-100 microfarads). By scaling the electrometer feedback capacitor to the CDL, system noise can be maintained constant while greatly increasing system bandwidth. Since signal density increases with decreasing jet ID, the cell with much smaller components becomes both more sensitive and faster. Sensitivity can be traded off for bandwidth or vise versa. As an example, existing commercial detectors are capable of just detecting a peak concentration of 1.5E-11 grams/milliliter in a peak 67 seconds wide at the base, while the present invention has been used to detect 4.3E-12 grams/milliliter peak concentrations on a peak 6.7 seconds wide at the base when both detectors are operated at a volumetric flow rate of 1.2 milliliters/minute with a signal to noise ratio (S/N) of 3. If the RC time constant of conventional detectors is decreased significantly to allow detection of narrower peaks the system noise increases sharply resulting in a much higher minimum detectable peak concentrations (lower S/N ratio) in contrast with the present invention.

Cleaning of the WE electrode is achieved by using metal electrodes such as platinum, nickel, gold or other metals with a unique pulsed potentiostat. The potentiostat applies a fast periodic waveform which strongly oxidizes, then strongly reduces the surface of the WE and/or the solvent with short duration pulses. The time scale is such that reaction products are not permitted to achieve significant surface coverage or interaction. During oxidation, oxygen intermediates are strongly adsorbed. Since other species are substantially less concentrated, the high concentration of solvent and solvent reaction products tend to displace other species on the electrode surface. Microbubbles of oxygen gas also tend to form which tend to lift and disrupt partial films. On a microscopic scale, the electrode surface seems to swell due to the significant quantity of oxygen atoms associating with the metal atoms of the electrode surface (up to two oxygens per metal atom). Further, a small quantity of metal atoms dissolve from the surface into the solution. Apart from these physical means of preventing film formation, the strongly oxidizing condition at the electrode surface may favor further direct electrochemical oxidation of the potentially fouling species or reactive intermediates of the solvent oxidation and provide alternate mechanisms to deactivate or further react the offending species. When the electrode potential is changed to strongly reducing conditions, the intermediates to oxygen formation are reduced or desorbed, some dissolved metal redeposits and the electrode surface tends to recrystallize. Hydrogen tends to adsorb on the electrode which appears to the solution as much more metallic. The objective of the oxidation and subsequent reduction is not necessarily to create a pure metal surface but a reproducible metal/metal oxide surface, since the objective is electrochemical analysis, not mechanistic surfaces studies.

During this cleaning sequence, very large currents flow compared to the analytical currents of interest. It is important to match the electronic controller characteristics to the cell and to optimize the cell for pulsed operation in order for the cell to be fast, but also so as not to saturate the electronics or limit the reactions due to current or voltage limits. The cleaning pulses can be looked at as though a fixed charge is injected for each of the pulses. When the electrode is pulsed to a working potential, cleaning currents and charging currents decay very rapidly to allow measurement of the small analytical signal. This decay is very reproducible.

The cleaning pulses can be employed in reverse order to obtain a more metal oxide like electrode surface. Since the time spent at the working (measuring) potential is short, reaction products tend not to build up on the electrode. The two cleaning pulses in reverse order use the same mechanisms for cleaning but make the analytical measurement on different types of surfaces. The cleaning pulse immediately preceding the working potential may also pre-oxidize or pre-reduce (depending on its polarity) some part of the sample to enhance or modify the measurement.

Both the normal and reverse cleaning method may produce catalytic surfaces changing the reaction potentials of some normally difficult to react species to much lower potentials compared to those required using DC applied potentials. A good example of this is the easy oxidation of short chain alcohols at potentials as low as +0.4 V versus a Ag/AgCl (3M KCl) reference electrode.

The cleaning mode can prevent fouling of even very high concentrations of fouling species. Phenol is well known as a very bad film former. In a detector operated in the DC mode, as few as three 500 nanograms/5 microliter injections will decrease response by as much as 50%. In the cleaning mode, no change in response is observable even after 350 similar injections. Raw urine treated by adding KOH to precipitate proteins has also been directly injected into a chromatograph. Such a sample typically contains tens of micrograms of offending species which conventionally completely foul the WE in one injection. In the cleaning mode, no decrease in response is observed after 10 injections.

In addition to the uses described above, the invention also provides for advances in other electrochemical techniques due to superior hydrodynamics, response time, and signal to noise ratio while maintaining very low response volume. The metal WE can be replaced with carbon based electrodes such as glassy carbon, carbon-epoxy mixtures or carbon fiber-epoxy bundles, the cross sectional areas of which are similar to the metal working electrode. Although large potential steps and the cleaning modes described above may be inappropriate using these materials, small fast potential steps (i.e., 2 to 50 millivolts in 1 microsecond to 100 milliseconds) can be used which yield both quantitative and qualitative information on components in flowing streams. A major advantage of these materials is in extending the cathodic potential region available for organic reductions. The carbon based electrodes are also appropriate base materials on which to deposit or plate thin films of mercury. Such films can act as pure mercury electrodes allowing the use of mercury specific electrochemical reactions, such as anodic stripping of heavy metals, cathodic stripping of halides and sulfur species reactions among others.

DETAILED DESCRIPTION OF THE INVENTION

Figure 1:
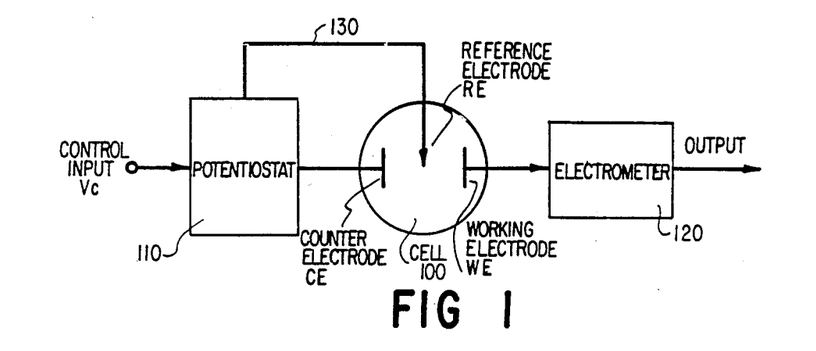
FIG. 1 shows a block diagram of an electrochemical detector with a three electrode electrochemical cell.

The present invention is a unique electrochemical detector in which each of the individual building blocks of a conventional detector shown in FIG. 1 has been redesigned. The result is a detector with very fast response time on the order of 10 milliseconds or faster which is ideally suited for the analysis of flowing streams with low flow rates on the order of 0.025 to 10 milliliters/minute such as in high performance liquid chromatography. The particular embodiment shown is optimized for a three electrode wall-jet flow through system, but as will be obvious, many of the individual facets of the present invention are also applicable to two electrode systems, flow through cells which do not incorporate wall-jets such as thin layer cells, as well as static, non-flow through cells. In other words, the present invention is applicable to any electrochemical detector system where it is desirable to maximize response, prevent changes in response of the working electrode over time, greatly reduce the need for the use of internal standard calibration, prevent passivating film formation (i.e., fouling) of the working electrode, greatly reduce the need to periodically disassemble the electrochemical cell, increase the dynamic range of the detector by better potential control and lower noise, or reduce the response time so as to measure rapidly changing electrochemical events or make multiple measurements in a short period of time.

Figure 2:
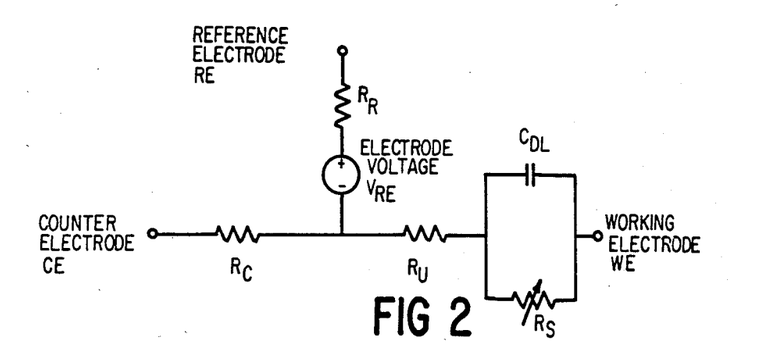
FIG. 2 shows an electrical model of an equivalent circuit for the electrochemical cell as in FIG. 1.

It is necessary in the present invention that the electrochemical cell 100 as shown in FIG. 1 for a three electrode detector and its equivalent circuit as shown in FIG. 2 have a fast response time to changes in potential and that the electrodes respond reproducibly and rapidly to potential changes. Existing electrochemical flow cells are relatively slow with long time constants for several reasons. First, since the in-situ cleaning of the working electrode WE has previously proven either partially or totally ineffective, having larger electrodes have provided a longer period of time during which there is some cell response. However, such large electrodes have a large equivalent electrical capacitance CDL as shown in FIG. 2 which is proportional to the total electrode surface area and is in the range of 10–100 microfarads or greater. The result is that such large electrodes are either very slow electrically or require large current sources for charging the cell from the potentiostat 110 in FIG. 1. Second, also because of the ineffectiveness of the electrode cleaning, many workers have gone to glassy or vitreous carbon working electrodes WE which are not as rapidly fouled. Unfortunately, carbon electrodes have very long surface chemistry equilibration times on the order of several minutes as well as nonreproducible surface states when subjected to varying potentials. A similar problem occurs with metal electrodes in the prior art, since there are associated surface chemistry reactions due to fouling also on the order of several minutes. Finally, previous workers have generally placed the reference electrode RE some distance from the working electrode WE, thus causing the uncompensated resistance RU in FIG. 2 between the reference electrode RE and the working electrode WE to be in the range of 100–1000 ohms or greater. Thus, the potentiostat 110 of FIG. 1 must also be capable of relatively high voltage outputs (10–100 volts) as well as high current outputs (greater than 1 ampere) in order to rapidly change potential up to several volts then make a current measurement in under 100 milliseconds, which prohibits the use of high performance, low noise, small signal amplifiers for constructing a high speed potentiostat 110.

An identical series of problems also exist for a high speed two electrode cell system in which the reference electrode RE of FIG. 1 is used in place of the CE.

Figure 3:
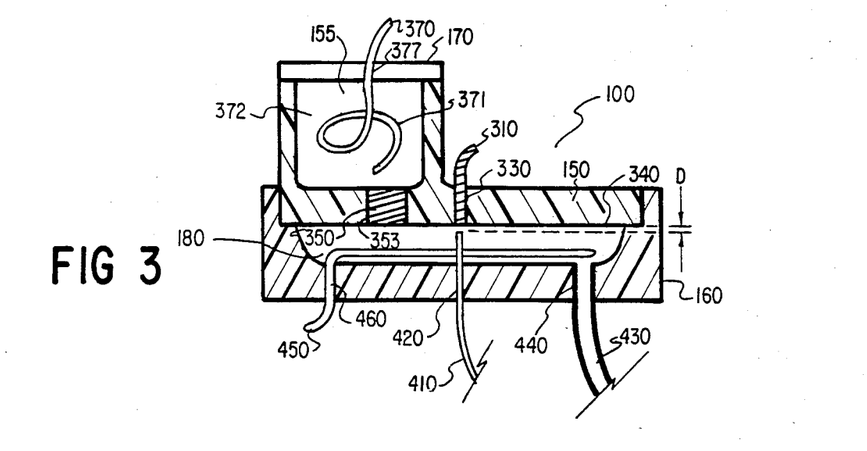
FIG. 3 shows a cross-sectional view of an assembled electrochemical cell according to a preferred embodiment of the present invention.

FIG. 3 shows a cross section of the electrochemical cell 100 used in the present invention and FIGS. 4A, 4B, 5A, 5B, 6A and 6B show the individual structural members used in the cell 100 of FIG. 3. The structural members shown in FIGS. 4A, 4B, 5A, 5B, 6A and 6B of cell 100 are constructed of a suitable material such as polythylene, polypropylene, or teflon which is not affected by the chemicals flowing through the cell 100. Typical dimensions for the members shown in FIGS. 4A, 4B, 5A, 5B, 6A and 6B are shown in Table 1, below.

Table 1

Figure 6A:
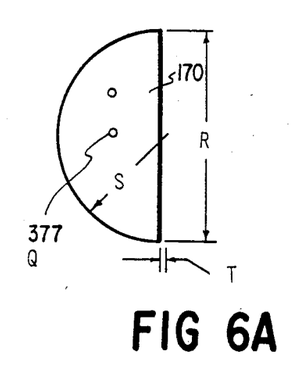
FIGS. 6A and 6B show a top and side view of a reference compartment cover for use in constructing the electrochemical cell of FIG. 3.
Figure 6B:
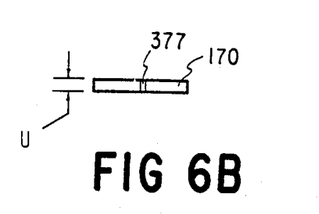

A = 1.2 mm
B = 0.75 mm
C = 1.2 mm
D = 1.2 mm
E = 25 mm
F = 8 mm
G = 2 mm
H = 0.75 mm diameter
I = 1.6 mm diameter
J = 0.25 mm diameter
K = 23 mm
L = 25 mm
M = 27 mm
N = 6 mm
O = 4 mm
P = 2 mm
Q = 0.75 mm diameter
R = 25 mm
S = 13 mm radius
T = 1.2 mm
U = 1.2 mm. The working and reference electrode holder 150 of FIGS. 4A and 4B is positioned into the jet holder 160 of FIGS. 5A and 5B and a reference compartment cover 170 shown in FIGS. 6A and 6B is used to cover a reference compartment 155 in the working and reference electrode holder 150 to form cell 100 of FIG. 3 with a main cell cavity 180 with a total internal volume of approximately one milliliter.

Figure 4A:
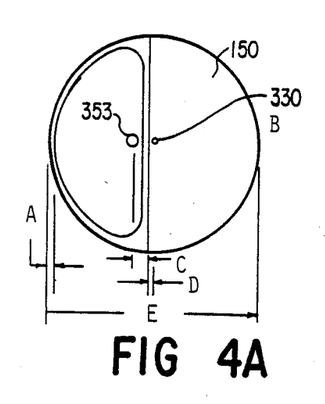
FIGS. 4A and 4B show a top and side view of a jet holder for use in constructing the electrochemical cell of FIG. 3.
Figure 4B:
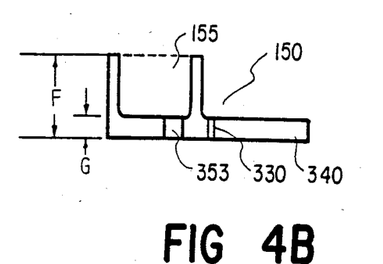
Figure 5A:
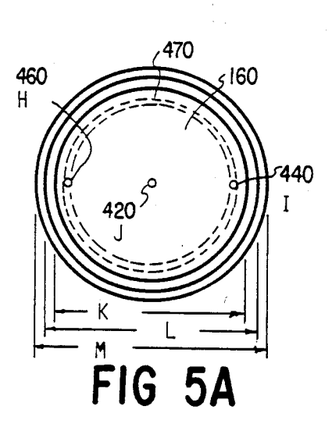
FIGS. 5A and 5B show a top and side view of a working and reference electrode holder for use in constructing the electrochemical cell of FIG. 3.
Figure 5B:
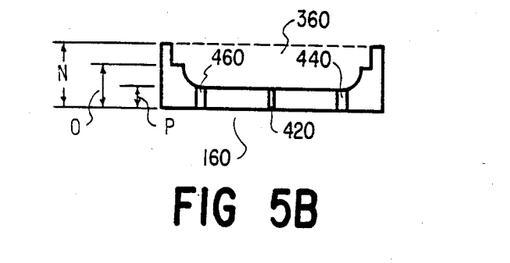

A small diameter metal working electrode 310 is inserted in the working and reference electrode holder 150 as shown in FIGS. 4A and 4B through a hole 330 so that the end of working electrode 310 is flush with the inner surface 340 of the working and reference electrode holder 150 as shown in FIG. 3. The working electrode is typically made of platinum wire with an outer diameter of 0.079 millimeters, and a surface area of 0.0044 square millimeters. The equivalent electrode capacitance CDL as shown in the cell model of FIG. 2 due to a double layer interaction of the working electrode and the fluid in the cell cavity 180 is kept small since the double layer capacitance CDL is proportional to the surface area of the working electrode WE. Thus, for a working electrode WE as described for use in FIG. 3 (0.0044 square millimeters) the equivalent double layer capacitance CDL when the cell is filled with liquid will be on the order of 0.1-0.2 microfarads or less, rather than 10-100 microfarads or greater as in the prior art. In addition, as will be explained shortly, when dynamically cleaned according to the present invention, the small metal working electrode WE is not fouled.

A porous plug 350 made of suitable material such as porous ceramic or plastic is inserted in hole 353 in electrode holder 120 and flush with inner surface 340 forming a liquid junction which acts like a wick for electrochemical communication between the main cell cavity 180 and a reference electrode 370. The porous plug and construction of a suitable reference electrode 370 is well known in the art and, for example, consists of a silver wire 371 coated with silver chloride and submerged in a silver saturated solution of 3M potassium chloride 372. The potassium chloride solution is held in reference compartment 155 which is part of electrode holder 150 and is covered by the reference compartment cover 170 as shown in FIGS. 6A and 6B. The silver wire 371 passes out of the reference compartment 155 via hole 377. The reference electrode 370 constitutes an electrode voltage source VRE in series with equivalent reference resistance RR as shown in the cell model of FIG. 2. The actual values of VRE and RR will be on the order of 0-1.0 volts and 1K-100K ohms respectively depending on the particular reference cell 370 chemistry and the eluent in the main cell cavity 180. The porous plug hole 353 is placed as close as possible (i.e., between 0.25 and 2.5 millimeters) to the reference electrode hole 330. By minimizing the distance between holes 353 and 330, the uncompensated cell resistance RU between the reference RE and working electrode WE as shown in the cell model of FIG. 2 is kept to a minimum, well below 100 ohms when the eluent in the main cell cavity 180 is for example a 0.1M potassium nitrate solution rather than 100-1000 ohms as in the prior art.

A drawn capillary tube 410 with an internal diameter of about 10-300 micrometers is inserted through an inlet hole 420 directly in line with hole 330 to within a distance D of inner surface 340 that is between 0.25 and 20 times the inner diameter of the drawn capillary tube 410 (i.e., 0.025 to 2 millimeters with a 0.1 millimeter diameter tube). The capillary tube 410 thus serves as both an inlet transfer line to the cell 100 and as a jet which protrudes into cavity 180 with true wall-jet hydrodynamics for a small diameter jet in contrast to the large diameter tubes explained by J. Yamada and H. Matsuda in "Wall Jet Electrodes", Electroanalytical Chemistry and Interfacial Electrochemistry, 44, p. 189 (1973). The very small diameter tube 410 not only guarantees the optimum interaction between the eluent and the working electrode 310 but also produces a very small effective cell dead volume of between 3 nanoliters and 3 microliters which is necessary for modern LC analysis.

The relationship between cell response, i(lim), and the fluid cell parameters for true wall-jet cells is:

$$i(lim) = 1.60 \, knFD^{\frac{2}{3}} v^{-5/12} V^{\frac{3}{4}} a^{-\frac{1}{2}} R^{\frac{1}{4}} C_o$$

where:

k = constant approximately = 1
n = Equivalents/Mole
F = Faraday const. = 96500 amp-sec/Eq
D = Diffusion Coef. = 1 E-5 sq cm/sec
v = kinematic viscosity = 9 E-3 sq cm/sec
V = Vol. Flow Rate = 0.029 ml/sec
a = jet inner dia., cm
R = working Electrode Radius, cm
Co = Conc. Analyte, Moles/ml Previous workers have assumed that small working electrodes 310 were hydrodynamically undesirable since the theoretical relationship shown above was no longer followed for R < 1.5 millimeters. A primary reason for this mistaken assumption concerning small working electrodes is the difficulty in making very small jets (a < 0.3 millimeters). In order to maintain wall jet hydrodynamics to avoid plugging and to keep pressure drop across the jet tube 410 to a minimum, the technique used in jet production is very important. In addition, in order to provide optimum true wall-jet performance with very small jet tubes 410 and very small working electrodes 310 it is important to control three parameters: (1) the working electrode radius to jet inner diameter ratio (R/a); (2) the aspect ratio (outer diameter A divided by inner diameter a) of the jet tube 410; and (3) the internal smoothness of the jet tube 410. The lower limit of true wall-jet hydrodynamics is approached when R/a is equal to or greater than 4. Thus, when R/a = 4, the smallest possible electrode is used for a given jet ID yielding maximum average current density and minimum noise.

To properly control these parameters for a very small jet, the present invention makes use of a drawn capillary tube 410 to form the jet. The capillary tube 410 may be made either of fused silica or glass so long as the resultant tube has a very smooth inner surface with surface features less than 1000 Angstroms in size. Because drawn tubing is used, it is possible to reduce both the inner diameter and the aspect ratio of the outer diameter to the inner diameter of the jet tube (A/a) below what can be achieved by drilling, which is specifically important for small diameter jets. To maintain good wall-jet hydrodynamics it is necessary that the aspect ratio of the jet tube 410 be less than or equal to 4 with an outer diameter A no greater than the IIIdiameter R of the working electrode 310.

The remainder of the cell shown in FIG. 3 comprises an exit tube 430 for the eluent made of the same material as structural members 150, 160 and 170 with an outer diameter of 1.6 millimeters inserted in effluent hole 440. Finally, a metal counter electrode 450 tyically made of platinum is inserted through a counter electrode hole 460 in the jet holder 160. The counter electrode 450 is typically made from the same material and diameter wire as the working electrode 310, but is wound around the base of the jet holder 160 as shown by dotted lines 470 in FIG. 4A. This creates an effective surface area for the counter electrode 450 at least 50 times the surface area of the working electrode 310. The symmetrical arrangement of the counter electrode 450 around the working electrode 310 insures a uniform electric field across the surface of the working electrode 310 provided the counter electrode 450 is separated from the working electrode 310 by at least three times the distance separating the working electrode 310 and the porous plug 350 forming the inlet for the reference electrode 370.

Figure 7:
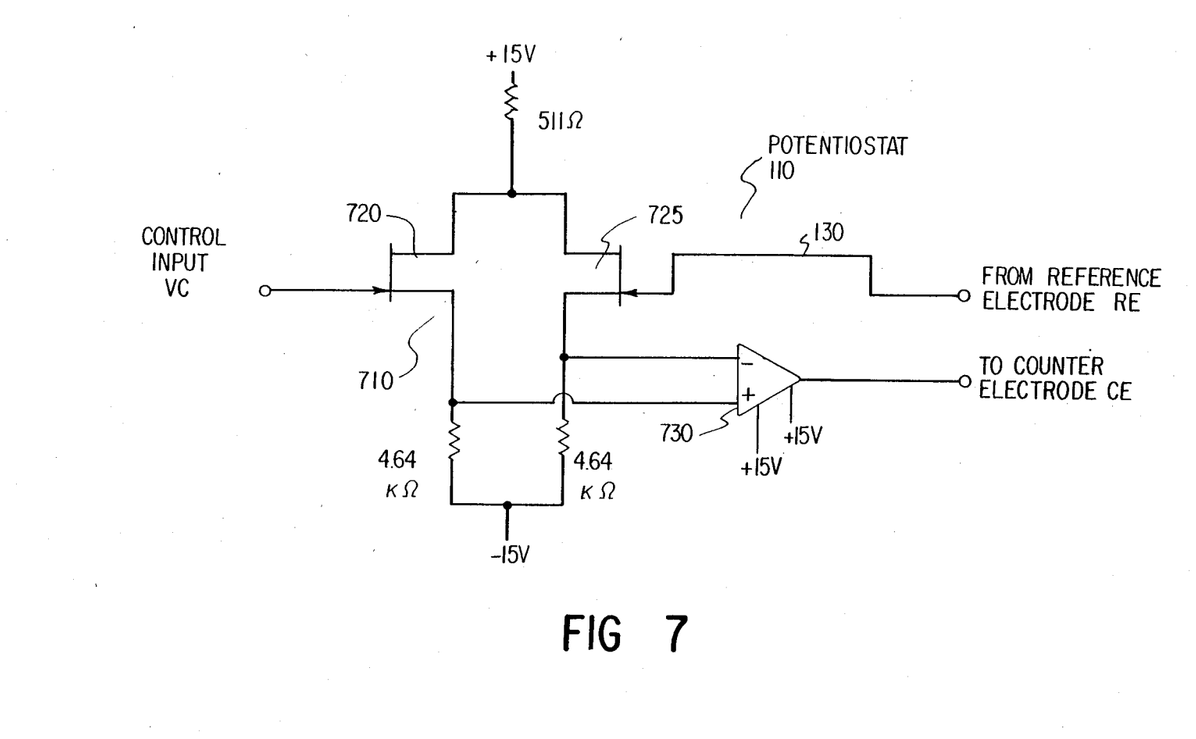
FIG. 7 shows a potentiostat for use as in FIG. 1.

FIG. 7 shows a schematic for potentiostat 110 as used in the detector in FIG. 1. The potentiostat 110 provides the electrical potential between the counter electrode CE and the working electrode necessary to drive the electrochemical cell 100. The potentiostat 110 shown in FIG. 7 has a differential input for the reference electrode RE of cell 100 and a control input VC which provides the desired waveform to drive the cell 100. The cell 100 and potentiostat 110 form a unity gain buffer amplifier feedback loop 130 via the reference electrode RE so that the resistances RC and RR and voltage VRE as shown in the cell model of FIG. 2 are inside the feedback loop 130. Thus the actual values of RC, RR, and VRE do not affect the detector performance. Hence, only the uncompensated cell resistance RU and the double layer capacitance CDL must be optimized as explained above. When the time constant as determined by RU and CDL is made short enough (i.e., less than 1 millisecond) as in the present example, a 10 millisecond control input VC applied to the potentiostat 110 will also be applied to the cell 100 with essentially no time constant distortion. A longer time constant as high as 10 milliseconds can be accommodated by increasing the control input period to 20 milliseconds with only a small reduction in waveform precision.

The potentiostat 110 is composed of a high impedance input 710 shown in FIG. 7 as dual FETs 720 and 725 coupled to a low noise, small signal operational amplifier 730. Since the double layer capacitance CDL is kept well below 10 microfarads and Ru is in the range of 10–100 ohms, amplifier 730 need only be capable of sourcing low output currents (i.e., 10–20 milliamps) and still be able to drive the cell 100 coupled directly to the output of amplifier 730 to the necessary 1–2 volts in under 1 millisecond.

The control input VC of potentiostat 110 is any of a number of possible waveforms as shown for example in FIGS. 8A, 8B, 9A and 9B. As shown in the normal cleaning mode of FIG. 8A, the working electrode WE is pulsed to a voltage Eox great enough to cause the metal electrode and the solution to oxidize for a short period of time Tox, then pulsed to an opposite reducing voltage Ered where the electrode is reduced for a short period Tred, then set to the desired working voltage Ework for a period Tw to measure the faradaic current of interest. The entire cycle is then repeated over and over again. Typical values for the necessary voltages when for example the eluent is a solution of 0.1M potassium nitrate and the working electrode WE is platinum is:

Eox = +1.85 v

Ered = −1.00 v

Figure 8A:
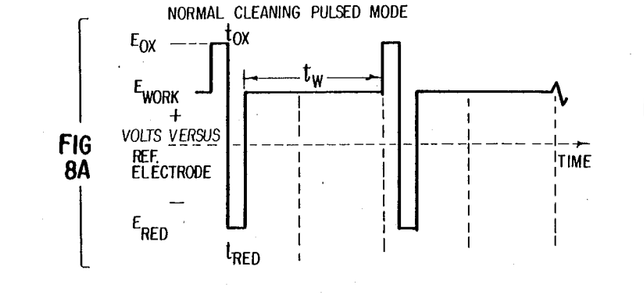
FIGS. 8A and 8B show the waveforms for the normal and reverse cleaning pulsed modes and FIG. 8C is the current measurement waveform according to the present invention.

Ework = +1.10 v versus the silver/silver chloride (3 m KCl) reference electrode 370, and the time periods are:

Tox = tw/4 to tw/20

Tred = tw/4 to tw/20

Tw = 10–800 milliseconds

The sum of Tox+Tred+Tw is thus less than or equal to 1.2 seconds.

Figure 8B:
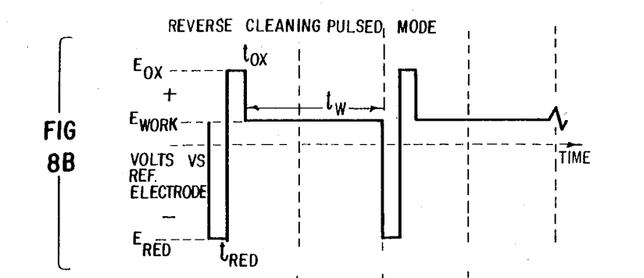
Figure 9A:
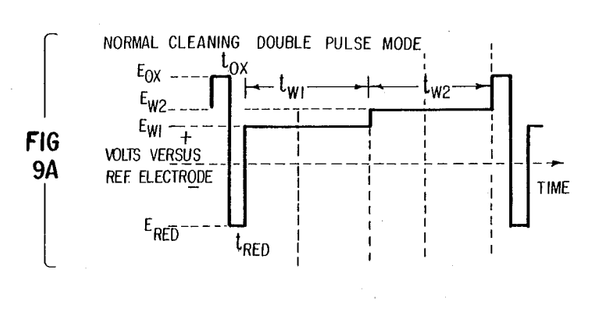
FIGS. 9A and 9B show the waveforms for the normal and reverse cleaning double pulse modes and FIG. 9c is the current measurement waveform according to the present invention.
Figure 9B:
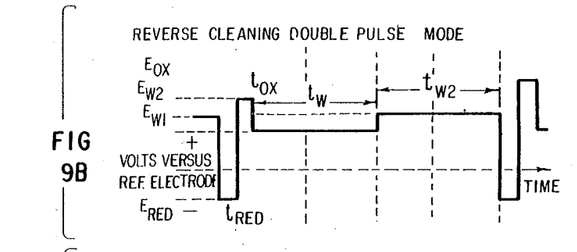

A reverse cleaning mode as shown in FIG. 8B can also be employed in which Ered precedes Eox. Double pulsing of the working potential to two or more measurement voltages (Ew1 and Ew2) as shown in FIGS. 9A and 9B is also possible in either the normal or reverse cleaning modes respectively as desired for a multiple potential electrochemical analysis. The periods Tox, Tred and Tw in the double pulsing modes are the same as in the normal pulsing modes.

During Tox not only is oxygen produced on the metal electrodes, but the electrode surface area will increase. Then, during Tred, hydrogen is produced on the electrode, the metal is recrystallized, and the electrode shrinks in size causing both mechanical and chemical cleaning to occur. It is not absolutely necessary that the electrode surfaces be recrystallized to pure metal, only that the actual surface state be precisely reproducible. In addition, because this cleaning method is used on such a short time scale while surface fouling concentrations are still very low, the actual sensitivity of the detector may be increased in spite of the apparently violent nature of surface reactions that occur.

Figure 10:
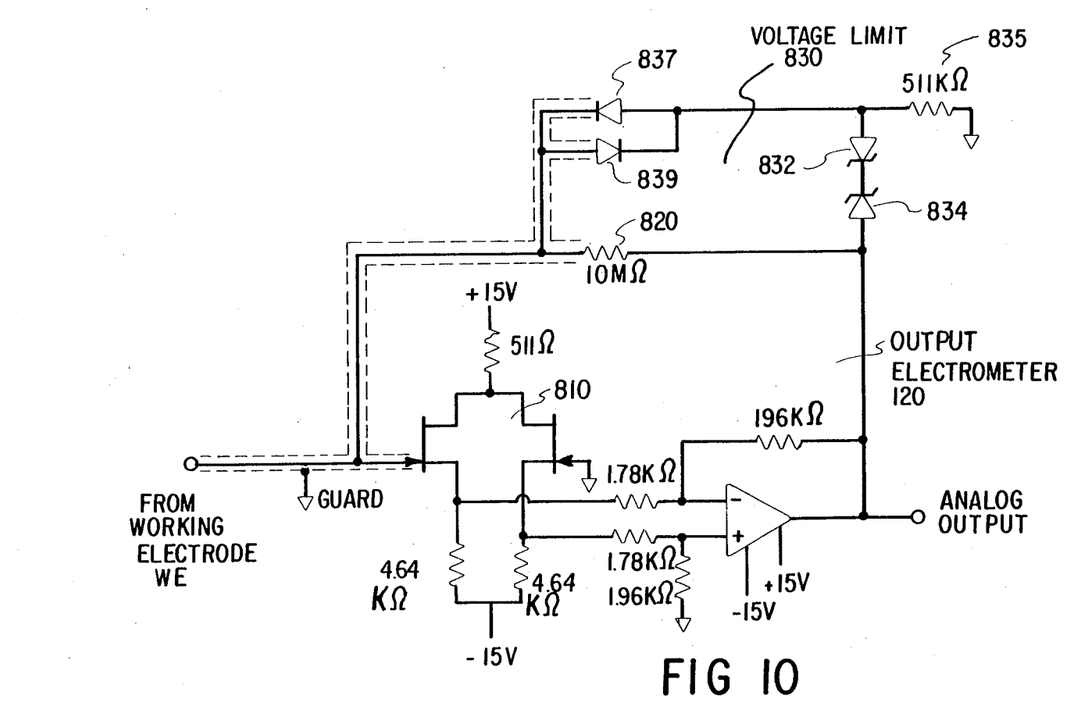
FIG. 10 shows an output electrometer for use as in FIG. 1.

The cell current out of the working electrode WE is measured by means of an electrometer 120 as shown in FIG. 1. The electrometer 120 is a high input impedance current-to-voltage amplifier as shown in FIG. 10. With a small working electrode WE as used in the present invention the faradaic current of interest modeled in FIG. 2 as variable resistor RS in parallel with the double layer capacitance CDL is in the range of 1 picoampere to 1 microampere. The electrometer 120 serves to provide a virtual ground potential for the working electrode WE so that the potentiostat 110 need not have a differential output. As shown in FIG. 10, the electrometer 120 is a modification of conventional designs with a dual FET front end 810 and a feedback resistor 820 which sets the current-to-voltage conversion scale. Particular effort is necessary in the choice of FET 810 and in guarding to reduce input voltage noise to less than or equal to 1 microvolt while maintaining input current noise to less than 10 femtoamps. A further modification of conventional electrometers includes moving the pole formed by the cell double layer capacitance and the feedback resistor 820 to a sufficiently high frequency to guarantee that the electrometer is unconditionally stable even with large changes in cell capacitance. Since the charging and discharging current of the double layer capacitance CDL also flows into the electrometer 120 a voltage limit circuit 83 is required to guarantee that the electrometer is fast enough to respond to the high speed cell currents. The voltage limit circuit 830 is coupled to the electrometer 120 between the analog voltage output and the input from the working electrode WE so that the electrometer 120 does not saturate while the cell capacitance CDL is charged or discharged. The voltage limit circuit 830 is comprised of two back to front series connected reference "zener" diodes 832 and 834 coupled to the electrometer output and a resistor 835 to bias the reference diodes 832 and 834 properly when the voltage limit 830 is activated. Two low leakage diodes 837 and 839 are coupled back to front in parallel with each other and are coupled between the reference diodes 832 and 834 and the electrometer input from the working electrode WE.

Figure 8C:
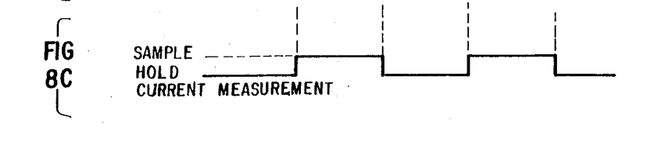
Figure 9C:
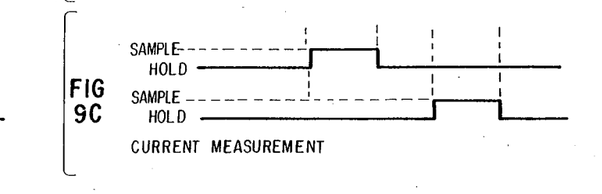

The actual measurement of the faradaic current by the electrometer 120 is done during the later portion of the period of the application of the working voltage as shown in FIGS. 8C and 9C. A further advantage of the present invention is that because the charging and discharging time of the double layer capacitance Cu is so short, a larger percentage of the total pulsed cycle is available for measuring the faradaic current during an analysis without introducing errors due to the capacitive current, thus increasing both the accuracy and the resolution of the detector. Since the electrometer 120 is very sensitive to its environment, for optimum performance (i.e., highest signal-to-noise ratio) it is desirable that the sampling periods shown in FIGS. 8C and 9C be synchronized with the frequency of the AC power line. For a 60 hertz power system this requires the sampling period be repeated at an integer multiple of 16.67 milliseconds.

What is claimed is:

1. A method of detecting the concentration of electrochemical species in a fluid with an electrochemical cell with a working electrode comprising:
   oxidizing the working electrode for a period less than or equal to 200 milliseconds;
   reducing the working electrode for a period less than or equal to 200 milliseconds;
   applying a working potential to the working electrode for a period less than or equal to 800 milliseconds; and
   measuring a current produced by electrochemical reactions on the working electrode at the working potential for integer multiples of a main power line period.

2. A method as in claim 1 further comprising:
   flowing the fluid through the electrochemical cell.

3. A method as in claim 1 further comprising applying a plurality of working potentials to the working electrode for a plurality of periods each less than or equal to 800 milliseconds.

4. A method of detecting the concentration of electrochemical species in a fluid with an electrochemical cell with a working electrode comprising a metal, said method comprising:
   oxidizing the working electrode for a first period less than or equal to 200 milliseconds so that the surface area of the working electrode increases;
   reducing the working electrode for a second period less than or equal to 200 milliseconds so that the surface area of the working electrode decreases;
   applying a working potential to the working electrode for a third period less than or equal to 800 milliseconds, and
   measuring a current produced by electrochemical reactions on the working electrode at the working potential.

5. A method as in claim 4 further comprising applying a plurality of working potentials to the working electrode for a plurality of periods each less than or equal to 800 milliseconds.

6. A method as in claim 4 wherein the first and second periods are applied in reverse order.

7. A method as in claim 4 further comprising flowing the fluid through the electrochemical cell.

8. A method as in claim 4 comprising:
   further oxidizing the fluid during the first period to produce oxygen bubbles on the working electrode; and
   further reducing the fluid during the second period to produce hydrogen bubbles on the working electrode.

9. A method as in claim 8 further comprising applying a plurality of working potentials to the working electrode for a plurality of periods each less than or equal to 800 milliseconds.

10. A method as in claim 8 wherein the first and second periods are applied in reverse order.

11. A method as in claim 8 further comprising flowing the fluid through the electrochemical cell.

* * * * *